United States Patent [19]

Mase et al.

[11] Patent Number: 4,655,901
[45] Date of Patent: Apr. 7, 1987

[54] OXYGEN SENSOR ELEMENT

[75] Inventors: Syunzo Mase, Ama; Shigeo Soejima, Nagoya, both of Japan

[73] Assignee: NGK Insulators, Ltd., Japan

[21] Appl. No.: 635,914

[22] Filed: Jul. 30, 1984

[30] Foreign Application Priority Data

Aug. 9, 1983 [JP] Japan ................... 58-144477

[51] Int. Cl.⁴ ............................. G01N 27/46
[52] U.S. Cl. ................... 204/426; 204/425; 204/427; 204/429
[58] Field of Search ................ 204/18, 421–429

[56] References Cited

U.S. PATENT DOCUMENTS

| 4,282,080 | 9/1981 | Muller et al. | 204/195 S |
| 4,298,573 | 11/1981 | Fujishiro | 204/426 |
| 4,300,990 | 11/1981 | Maurer | 204/426 |
| 4,300,991 | 11/1981 | Chiba et al. | 204/426 |
| 4,384,935 | 5/1983 | De Jong | 204/426 |
| 4,402,820 | 9/1983 | Sano et al. | 204/429 |
| 4,416,763 | 11/1983 | Fujishiro | 204/426 |
| 4,502,939 | 3/1985 | Holfelder et al. | 204/429 |
| 4,505,806 | 3/1985 | Yamada | 204/426 |
| 4,505,807 | 3/1985 | Yamada | 204/426 |

Primary Examiner—T. Tung
Attorney, Agent, or Firm—Parkhurst & Oliff

[57] ABSTRACT

A measuring electrode is mounted on one side surface of a solid electrolyte, while a reference electrode is mounted on a separate solid electrolyte and disposed so as to face the opposite side surface of said one solid electrolyte across a gap.

9 Claims, 6 Drawing Figures

FIG_2

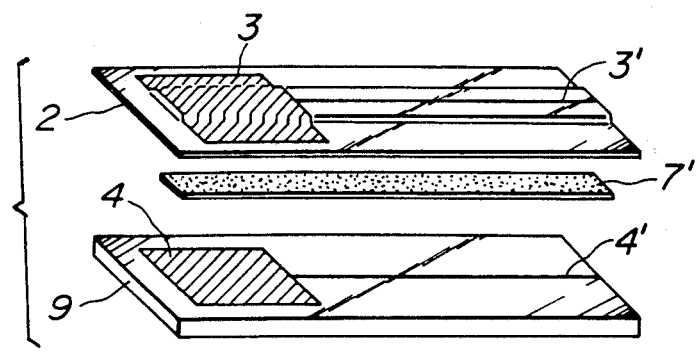
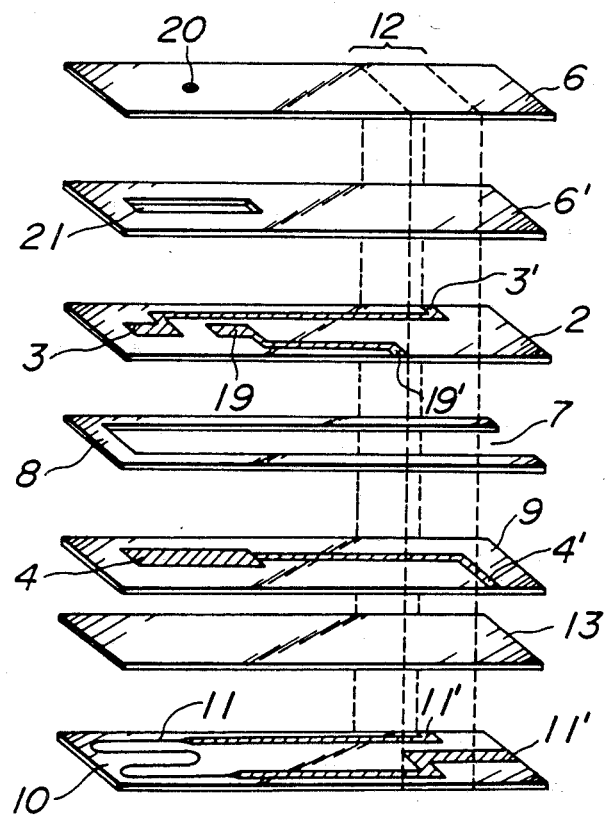

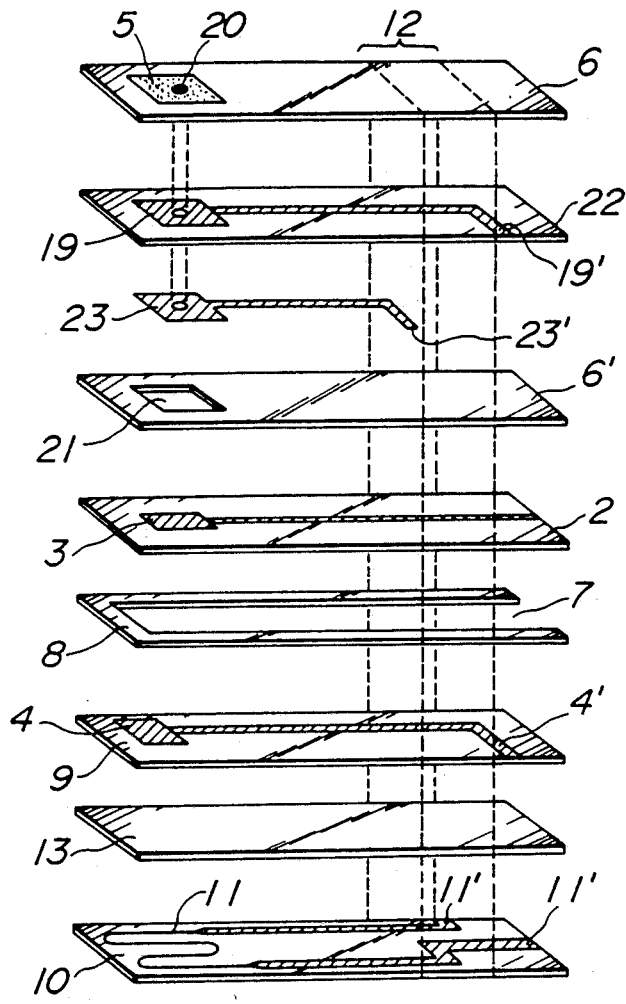
FIG_6

OXYGEN SENSOR ELEMENT

BACKGROUND OF THE INVENTION

1. Field of the Invention

This invention relates to an oxygen sensor element, and more particularly to an oxygen sensor element which detects oxygen concentration by using a concentration cell having electrodes carried by separate solid electrolytes.

2. Description of the Prior Art

Heretofore, for example, to detect oxygen concentration in automobile exhaust gas, various oxygen sensors have been used; namely, oxygen sensors having electrodes disposed on opposite surfaces of a cylindrical solid electrolyte, oxygen sensors having a built-in heater for ensuring regular operation even when exposed to low-temperature exhaust gas whose temperature is as low as below 300° C., or lean burn type oxygen sensors suitable for gas with an air-fuel ratio indicating excess air. As to the shape of the solid electrolyte in oxygen sensors, a cylindrical solid electrolyte with a bottom board and a laminated structure formed from plate-like or film-like solid electrolytes overlaid one above the other has been proposed and used.

The conventional arrangement of disposing a pair of electrodes on opposite surfaces of a film-like solid electrolyte has a shortcoming in that the difference in both the thermal expansion and the firing shrinkage between the solid electrolyte and the electrodes tend to cause stress in the solid electrolyte. When a sudden temperature change occurs or after continuous operation over a long period of time, various adverse effects result, such as the occurrence of cracks in the solid electrolyte, an increased error in the output electromotive force, or fracture of the oxygen sensor element. Such shortcomings are particularly noticeable in the case of thin film-like solid electrolytes.

FIG. 1 shows the structure of a laminated type oxygen sensor element according to the prior art, wherein film-like or plate-like solid electrolytes are overlaid one above the other, and a reference electrode 4 is spaced from a heater 11 by a gap portion 7 for introducing a reference gas such as air into the sensor element. Accordingly, the efficiency of heat transmission from the heater 11 to the reference electrode 4 is low, and the reduction of impedance between a solid electrolyte 2 and the reference electrode 4 is delayed, especially immediately after the start of the sensor operation. Thus, the structure of FIG. 1 has a shortcoming of being slow when beginning the sensing operation.

SUMMARY OF THE INVENTION

Therefore, a first object of the present invention is to provide an oxygen sensor element in which a solid electrolyte is prevented from cracking by suppressing the stress between the solid electrolyte and one or more electrodes tightly secured thereto.

A second object of the present invention is to provide an oxygen sensor element which is prevented from warping and cracking due to the difference in firing shrinkage between a solid electrolyte and electrodes attached thereto.

A third object of the invention is to provide an oxygen sensor element which has a built-in heater disposed in such a manner that heat from the heater is efficiently transmitted to a reference electrode, so as to ensure quick start of the sensor element by rapidly reducing its internal impedance at the start of its operation.

To fulfil the above-mentioned objects, an embodiment of the oxygen sensor element according to the invention has a first planar solid electrolyte carrying a measuring electrode mounted on one side surface thereof, and a second planar solid electrolyte is disposed in tight contact with that surface of the first planar electrolyte which is opposite to the measuring electrode. The second planar solid electrolyte has a gap portion adjacent the first planar solid electrolyte. A reference electrode is mounted on the surface of the second planar solid electrolyte at a position facing the first planar solid electrolyte across the gap portion.

In another embodiment of the invention, a heater, preferably a ceramic heater layer, is provided in the oxygen sensor element of the above-mentioned construction, which heater is tightly secured to the surface of the second planar solid electrolyte at a position separated from the reference electrode. For example, the ceramic heater layer is mounted in tight contact with that surface portion of the second planar electrolyte which portion does not carry the reference electrode.

There are three reasons why the invention utilizes the reference electrode mounted on the second planar solid electrolyte and the measuring electrode mounted on the first planar solid electrolyte.

The first reason is as follows: namely, if a reference electrode and a measuring electrode made of platinum or the like, are to be mounted on opposite surface of one planar solid electrolyte, the reference electrode is generally a cermet electrode which can be fired simultaneously with the green sheet of the planar solid electrolyte, while the measuring electrode is generally made of a similar cermet electrode as well, so that an oxygen sensor element with an excellent durability can be produced by sintering all of them simultaneously. Preferably, the planar solid electrolyte between the measuring electrode and the reference electrode should be thin, to reduce the impedance of the oxygen sensor element and to ensure proper operation at low temperatures.

However, when platinum electrodes or other cermet electrodes are disposed on opposite surfaces of one planar solid electrolyte, the difference in the coefficient of thermal expansion between the solid electrolyte and such electrodes results in a stress therebetween. Consequently upon the occurrence of sudden temperature change or after a continuous operation over a long period of time, the stress tends to cause cracks in the solid electrolyte. To reduce such stress, the first planar solid electrolyte avails only one side surface thereof for carrying one electrode, while the other electrode which contacts said one electrode is disposed on the second planar solid electrolyte. Thus, the stress on the first planar solid electrolyte is reduced to one-half, so as to prevent the first planar solid electrolyte from cracking.

The second reason is that when it is desired to produce a plate-like oxygen sensor having a reference electrode facing a central hollow portion and a measuring electrode disposed on one side surface thereof, the best result with a high durability is achieved, as a rule, by assembling component sheets through superposition of green sheets or printing, and then firing or sintering them simultaneously.

However, the firing shrinkage of the solid electrolyte generally differs from that of the cermet electrodes. Especially, if cermet layers for electrodes are applied to opposite surfaces of the first electrolyte green sheet, a very large difference in firing shrinkage occurs between the first solid electrolyte and the second solid electrolyte having no electrodes, resulting in possible warping and separation of solid electrolyte layers and cracks therein. To suppress such difference in firing shrinkage, the present invention uses different electrodes mounted on different solid electrolytes respectively, so as to obviate the above-mentioned shortcomings caused by such difference in firing shrinkage.

The third reason that the reference gas to be in contact with the reference electrode is air, in most cases, and platinum is accordingly widely used in as the reference electrode.

However, the activity of platinum is gradually reduced when it is heated in air over a long period of time, and an increasingly high temperature becomes necessary for ensuring the proper impedance level at the platinum electrode. On the other hand, the reduction of the activity of the measuring electrode due to exposure to engine exhaust gas is relatively small. Accordingly, the conventional oxygen sensor with a heater to heat its sensor element has a shortcoming in that the time necessary for starting the sensor by heating the reference electrode gradually increases as the sensor is used.

To shorten the time necessary for the heating up and to efficiently transmit heat from the heater to the reference electrode, the reference electrode and the heater are mounted on the same electrolyte, i.e., the second planar solid electrolyte, at different surface portions thereof. Whereby, the reference electrode is heated quickly to a high temperature.

In another embodiment of the invention, a porous ceramic or porous solid electrolyte is disposed in the gap portion facing the reference electrode. Whereby, the internal impedance of the oxygen sensor is reduced and the mechanical strength of the oxygen sensor element is improved by the presence of such porous ceramic or porous solid electrolyte in the otherwise hollow gap portion, while allowing effective contact of the reference electrode with the reference gas and without causing any adverse effects on the above-mentioned features of the invention.

An oxygen sensor element of the present invention may include a pair of electrodes forming an oxygen pump, and a DC voltage may be applied across such pair of oxygen pump electrodes to apply a direct current thereto. Whereby, an amount of oxygen proportionate to the amount of electric charge of the direct current may be moved from one electrode to the other electrode of the oxygen pump. At least one of the electrodes forming the oxygen concentration cell may be used in common with that of the oxygen pump.

BRIEF DESCRIPTION OF THE DRAWINGS

For a better understanding of the invention, reference is made to the accompanying drawings, in which:

FIG. 4 is an explanatory diagram of a practical example which is quoted in the description of the invention; and FIG. 5 and FIG. 6 are schematic exploded views of other embodiments of the oxygen sensor element according to the present invention.

Throughout different views of the drawings, 1 is an oxygen sensor element, 2 is a first solid electrolyte, 3 is a measuring electrode, 4 is a reference electrode, 3', 4' are lead wires with terminals, 5 is a porous ceramic layer, 6, 6' are gastight layers, 7 is a gap portion, 7' is a porous ceramics or solid electrolyte, 8 is a gastight solid electrolyte, 9 is a second solid electrolyte, 10 is a gastight layer, 11 is a heater, 11' is a lead wire with a terminal, 12 is a flange-engaging portion, 13 is an insulating layer, 19 is an electrode, 19' is a lead wire with a terminal, 20 is a diffusion hole, 21 is a cavity, 22 is a solid electrolyte, 23 is an electrode, and 23' is a lead wire with a terminal.

DESCRIPTION OF THE PREFERRED EMBODIMENTS

The invention will be described in detail by referring to FIG. 2 through FIG. 6 of the accompanying drawings.

Figure 1:
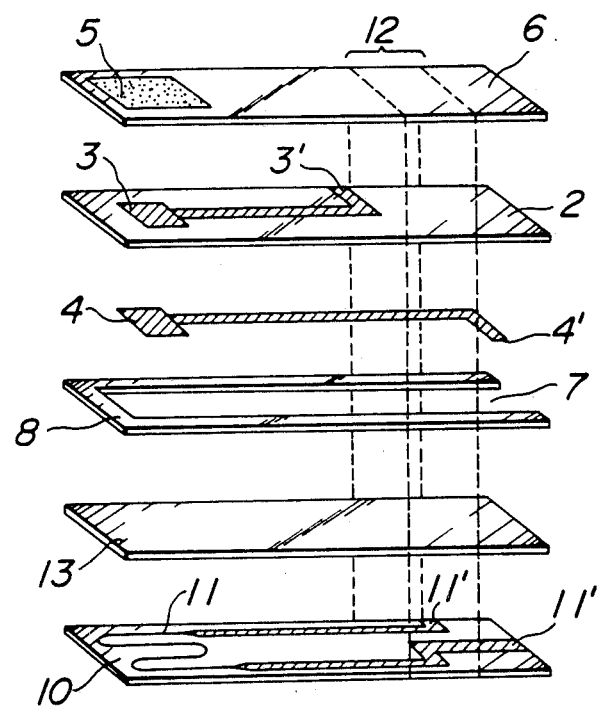
FIG. 1 is a schematic exploded view of a typical oxygen sensor element of the prior art.
Figure 2:
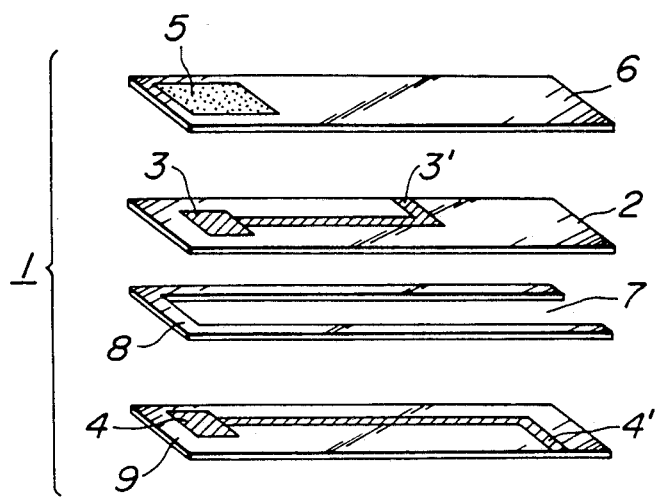
FIG. 2 and FIG. 3 are schematic exploded views of two embodiments of the oxygen sensor element according to the present invention.

FIG. 2 shows a schematic exploded view of an oxygen sensor element of laminated type made by using plate-like solid electrolytes, as an embodiment of the invention. In the illustrated oxygen sensor element 1, a first solid electrolyte 2 made of zirconia ceramics or the like, carries a porous measuring electrode 3 mounted on one side surface thereof, and the measuring electrode 3 is for instance made of platinum. A similar porous reference electrode 4 is mounted on one side surface of a second solid electrolyte 9. The first solid electrolyte 2 and the second solid electrolyte 9 are connected to each other with an intermediate solid electrolyte 8 disposed therebetween, so as to form an oxygen concentration cell.

The electrodes 3 and 4 have lead wires with terminals 3' and 4' connected thereto respectively, and the terminals 3' and 4' are disposed so as to be exposed to the outside of the oxygen sensor element 1. The measuring electrode 3 comes in contact with a gas being measured through a porous ceramic layer 5 made of, for example spinel. The porous ceramic layer 5 is enclosed by a gastight layer 6 made of zirconia or the like. The reference electrode 4 is exposed to a gap portion 7 defined in a gastight solid electrolyte 8. The gap portion 7 is surrounded by the first solid electrolyte 2, the second solid electrolyte 9, and non-gapped portion of the gastight solid electrolyte 8. A reference gas such as air is introduced in the gap portion 7.

Figure 3:
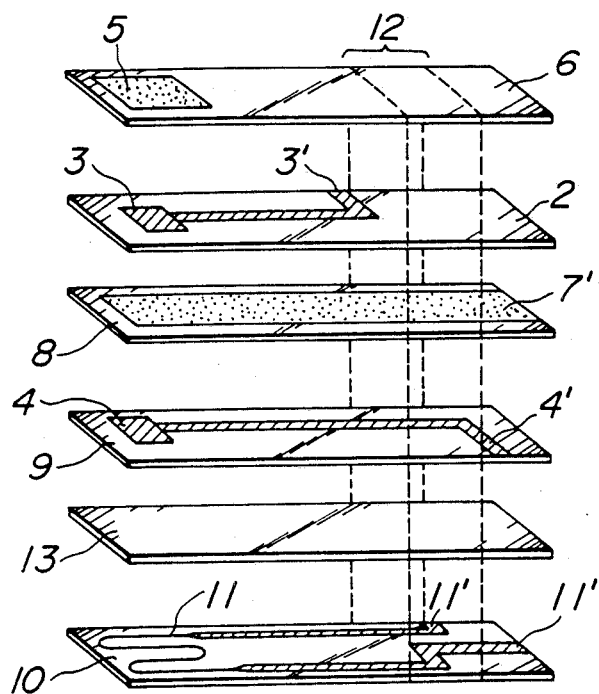

Instead of leaving the gap portion 7 hollow, a porous ceramic or solid electrolyte 7' may be fitted into the gap portion 7, as shown in FIG. 3. When the reference gas is fed into interstices of the porous ceramic or solid electrolyte 7', the reference electrode 4 comes in contact with the reference gas, and at same time, the impedance across the reference electrode 4 and the measuring electrode 3 is reduced by the presence of the porous ceramic or solid electrolyte 7', as compared with the case of leaving the gap portion 7 hollow. The porous ceramic or solid electrolyte 7' also acts to improve the mechanical strength of the oxygen sensor element 1 around the electrodes 3 and 4 thereof. The requirement for the porous ceramic or solid electrolyte 7' is to be pervious to the reference gas, and a preferable material is porous zirconia.

The embodiment of FIG. 3 has a gastight layer 10 carrying a heater 11 mounted on one side surface thereof. Opposite ends 11' of two lead wires for the heater 11 are disposed so as to be exposed to the outside at the surface of the oxygen sensor element 1. When assembled, the oxygen sensor element 1 can be mounted on a suitable flange (not shown) at a flange-engaging portion 12. The heat from the heater 11 is transmitted to the reference electrode 4 through an insulating layer 13 and the second solid electrolyte 9. The heater 11 can be heated by an alternating current (AC) or a direct current (DC). When DC is used, the gastight layer 10 and the insulating layer 13 are preferably made of alumina ceramics or other suitable insulating material. If only AC is used, the gastight layer can be made of solid electrolyte such as zirconia ceramics, and the insulating layer 13 may be dispensed with.

The embodiment of FIG. 3 is particularly useful in the case of using a DC power source, and in this case the insulating layer 13 provides a high insulation between the heater 11 and the reference electrode 4. To ensure good heat transmission, the thickness of the insulating layer 13 is preferably less than 50 μm.

From the standpoint of durability, the heater 11 is preferably made of a metal such as nickel, silver, gold, platinum, rhodium, palladium, indium, ruthenium, tungsten, molybdenum, an alloy thereof, and the like. However, electrically conductive ceramic compound such as zinc suboxide, lanthanum chromite ($LaCrO_3$), lanthanum boride ($LaB_6$), silicon carbide (SiC), and the like, can be also used to form a ceramic heater as the heater 11.

FIG. 4 shows a sample used in an experiment of the present invention. A 1.5 mm thick zirconia green sheet consisting of 96 mol % of zirconia ($ZrO_2$) and 4 mol % of yttria ($Y_2O_3$) was prepared for making the second solid electrolyte 9. Conductive layers for the reference electrode 4 and the lead wire and terminal 4' were printed on one side surface of the zirconia green sheet by using a cermet material consisting of 80% by weight of platinum and 20% by weight of zirconia ($ZrO_2$). A 50 μm thick paste layer of zirconia ceramics material for making the porous solid electrolyte 7' was printed thereon. A 50 μm thick zirconia material layer for the first solid electrolyte layer 2 was printed thereon by using a paste consisting of 96 mol % of zirconia ($ZrO_2$) and 4 mol % of yttria ($Y_2O_3$). Conductive layers for the measuring electrode 3 and the lead wire and terminal 3' were printed on the zirconia material layer by the same cermet material as that for the reference electrode 4.

The green body prepared by the above printings was fired at 1,400° C. for 2 hours, and an oxygen sensor element 1 according to the present invention was produced.

No cracks were found in the first solid electrolyte 2 of the thus produced oxygen sensor element 1. It was confirmed by tests that the oxygen sensor element 1 thus produced operated satisfactorily in engine exhaust gas at 400° C.

The formation of the oxygen sensor element of the invention is not restricted to the foregoing embodiments and example. FIG. 5 and FIG. 6 show structures of other embodiments or laminated structures made by overlaying a number of layers one above the other.

More specifically, the embodiment of FIG. 5 is the so-called lean burn type oxygen sensor element. In this embodiment, a first solid electrolyte 2 and a second solid electrolyte 9 are bonded to opposite surfaces of an intermediate gastight solid electrolyte 8, and a pair of electrodes 3, 4 forming an oxygen concentration cell and another pair of electrodes 19, 4 forming an oxygen pump are mounted on the solid electrolytes 2 and 9. The reference electrode 4 is used in common for both the oxygen concentration cell and the oxygen pump.

Gas to be measured is introduced into a cavity 21 through a diffusion hole 20 so as to come in contact with the measuring electrode 3. Due to the action of the oxygen pump, the oxygen partial pressure in the cavity 21 can be reduced to a level below that in the gas being measured at the outside of the oxygen sensor element 1. Having such oxygen pump incorporated therein, the oxygen sensor element of FIG. 5 can be used for the control of an engine which exhausts the so-called lean burn gas having a higher oxygen partial pressure than that of the theoretical air-fuel ratio.

FIG. 6 shows a modification of the oxygen sensor element of FIG. 5. In this modification, an oxygen concentration cell is made by using the solid electrolytes 2, 8, and 9 for holding the electrodes 3 and 4 in the same manner as the preceding embodiments, while an oxygen pump is made by using a completely separate set of electrodes 19 and 23 carried by a solid electrolyte 22 on opposite surfaces thereof. Lead wires with terminals 19' and 23' are formed on the opposite surface to the electrodes 19 and 23 as shown in FIG. 6. The function of the oxygen pump formed from the electrodes 19 and 23 across the solid electrolyte 22 is similar to what has been described above by referring to FIG. 5.

In the embodiments of FIG. 5 and FIG. 6, flange-engaging portions 12 fulfil the same function as the flange-engaging portion 12 of FIG. 3.

As described in the foregoing, an oxygen sensor element according to the present invention uses a measuring electrode and a reference electrode mounted on separate solid electrolyte layers, so that even if thin solid electrolyte layers are used to hold any of the electrodes, there is no risk of cracking of the solid electrolytes. Thus, the oxygen sensor element of the invention has a high reliability and is suitable for mass production.

Further, the oxygen sensor element of the invention has a heater facing the reference electrode only through a solid electrolyte layer without any gap, so that the heat from the heater is efficiently transmitted to the reference electrode. Accordingly, the impedance of the oxygen sensor element is quickly reduced by the heater, especially at the start of the sensor operation, so as to put the oxygen sensor into operation in a very short time while enabling a saving in power consumed at the heater.

Therefore, the oxygen sensor element of the invention is particularly suitable for detection and control of oxygen concentration in automobile exhaust gas, so that the oxygen sensor element of the invention is very useful in various industries producing exhaust gas.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen sensor element, comprising a first planar solid electrolyte having a first side surface and a second side surface, wherein a measuring electrode is mounted on said first side surface thereof, a second planar solid electrolyte having a first side surface and a second side surface, wherein the first side surface of the second planar solid electrolyte is in electrochemical contact with the second side surface of said first planar solid electrolyte, said second side surface of said first electrolyte being opposite from said first side surface of said first electrolyte, a gap portion located between said second side surface of said first planar solid electrolyte and said first side surface of said second planar solid electrolyte, said gap portion for carrying a reference substance, and a reference electrode mounted on said first side surface of said second planar solid electrolyte at a position facing said first planar solid electrolyte across said gap portion, said measuring electrode and said reference electrode forming an oxygen concentration cell for detecting the concentration of oxygen which communicates with said measuring electrode, such that said second side surface of said first planar solid electrolyte and said second side surface of said second planar solid electrolyte do not have any electrodes disposed thereon.

2. An oxygen sensor element, comprising a first planar solid electrolyte having a first side surface and a second side surface, wherein a measuring electrode is mounted on said first side surface thereof, a second planar solid electrolyte having a first side surface and a second side surface, wherein the first side surface of the second planar solid electrolyte is in electrochemical contact with the second side surface of said first planar solid electrolyte, said second side surface of said first electrolyte being opposite from said first side surface of said first planar solid electrolyte, a gap portion located between said second side surface of said first planar solid electrolyte and said first side surface of said second planar solid electrolyte, said gap portion for carrying a reference substance, a reference electrode mounted on said first side surface of said second planar solid electrolyte at a position facing said first planar solid electrolyte across said gap portion and a ceramic heater disposed in thermal contact with a surface of said second planar solid electrolyte at a position separated from said reference electrode, said measuring electrode and said reference electrode forming an oxygen concentration cell for detecting the concentration of oxygen which communicates with said measuring electrode, such that said second side surface of said first planar solid electrolyte and said second side surface of said second planar solid electrolyte do not have any electrodes disposed thereon.

3. An oxygen sensor element as set forth in claim 2, wherein said ceramic heater is disposed in thermal contact with said second side surface of said second planar solid electrolyte.

4. An oxygen sensor element as set forth in claim 1, 2, or 3 and further comprising a porous ceramic filled in said gap portion.

5. An oxygen sensor element as set forth in claim 1, 2, or 3 and further comprising a porous solid electrolyte filled in said gap portion.

6. An oxygen sensor element comprising:
a first planar solid electrolyte having a first side surface and a second side surface, wherein a measuring electrode is mounted on said first side surface thereof;
a gastight solid electrolyte having a gap portion defined therein, a first side surface of said gastight solid electrolyte being in electrochemical contact with said second side surface of said first planar solid electrolyte;
a second planar solid electrolyte having a first side surface and a second side surface, wherein a reference electrode is mounted on said first side surface thereof, said first side surface of the second planar solid electrolyte being in electrochemical contact with the second side surface of said gastight solid electrolyte, thereby forming a gap portion between said second side surface of said first planar solid electrolyte and said first side surface of said second planar solid electrolyte, said measuring and said reference electrode forming an oxygen concentration cell for detecting the concentration of oxygen which communicates with said measuring electrode, such that said second side surface of said first planar solid electrolyte and said second side surface of said second planar solid electrolyte do not have any electrodes disposed thereon.

7. An oxygen sensor as set forth in claim 6, wherein a ceramic heater is disposed in thermal contact with the second side surface of said second planar solid electrolyte.

8. An oxygen sensor element as set forth in claim 6, wherein a porous ceramic is filled in said gap portion.

9. An oxygen sensor element as set forth in claim 6, wherein a porous solid electrolyte is filled in said gap portion.

* * * * *